(12) United States Patent
Tobia et al.

(10) Patent No.: US 6,371,113 B1
(45) Date of Patent: Apr. 16, 2002

(54) ZERO FLOW PAUSE DURING VOLUME VENTILATION

(75) Inventors: Ronald L. Tobia, Sun Prairie; Steven K. Somerson, Madison, both of WI (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 08/916,553

(22) Filed: Aug. 22, 1997

Related U.S. Application Data

(60) Provisional application No. 60/027,613, filed on Oct. 10, 1996.

(51) Int. Cl.$^7$ ............................................. A61M 16/00
(52) U.S. Cl. ............................. 128/204.23; 128/204.21
(58) Field of Search ................... 128/204.18, 204.21, 128/204.23; 600/533

(56) References Cited

U.S. PATENT DOCUMENTS

| | | | | |
|---|---|---|---|---|
| 3,480,006 A | * | 11/1969 | Schomber ................... | 600/533 |
| 3,768,468 A | * | 10/1973 | Cox ....................... | 128/204.21 |
| 3,848,591 A | | 11/1974 | Smythe et al. .......... | 128/204.23 |
| 3,946,729 A | | 3/1976 | Hanna .................... | 128/204.23 |
| 4,031,885 A | | 6/1977 | Davis et al. ............... | 600/533 |
| 4,259,967 A | * | 4/1981 | Voren et al. ................ | 600/533 |
| 4,281,651 A | | 8/1981 | Cox ....................... | 128/204.23 |
| 4,318,399 A | | 3/1982 | Berndtsson ............ | 128/204.23 |
| 4,323,064 A | | 4/1982 | Hoenig et al. .......... | 128/204.21 |
| 4,393,869 A | | 7/1983 | Boyarsky et al. ...... | 128/204.18 |
| 4,444,201 A | | 4/1984 | Itoh ........................... | 600/529 |
| 4,802,492 A | * | 2/1989 | Grunstein ................... | 600/533 |
| 4,883,050 A | | 11/1989 | Urman et al. .......... | 128/202.27 |
| 4,982,735 A | | 1/1991 | Yagata et al. .......... | 128/204.23 |
| 5,048,515 A | * | 9/1991 | Sanso ..................... | 128/204.21 |
| 5,233,998 A | * | 8/1993 | Chowienczyk et al. ..... | 600/533 |
| 5,261,397 A | * | 11/1993 | Grunstein .............. | 128/204.23 |
| 5,303,700 A | | 4/1994 | Weismann et al. ..... | 128/204.23 |
| 5,315,989 A | * | 5/1994 | Tobia ..................... | 128/204.28 |
| 5,582,163 A | * | 12/1996 | Bonassa ................. | 128/204.26 |
| 5,630,411 A | * | 5/1997 | Holscher ............... | 128/205.24 |
| 5,647,351 A | * | 7/1997 | Weismann et al. ..... | 128/204.21 |

FOREIGN PATENT DOCUMENTS

| | | |
|---|---|---|
| DE | 33 06 607 A | 9/1983 |
| EP | 0 046 570 | 3/1982 |
| FR | 2 573 658 A | 5/1986 |
| GB | 2 077 444 A | 12/1981 |
| WO | 96 11717 | 4/1996 |

* cited by examiner

*Primary Examiner*—Aaron J. Lewis
(74) *Attorney, Agent, or Firm*—Andrus, Sceales, Starke & Sawall, LLP

(57) ABSTRACT

An improved system for making an accurate determination of the patient's compliance and airway resistance by ensuring that the flow to and/or from the patient at the end of a ventilator pause is, in fact, reduced to zero flow. The normal ventilator pause occurs at the end of an inspiratory cycle where the ventilator terminates the breathing air delivery to the patient and then enters a pause period. Values are taken for the airway flow and pressure at the beginning of the pause period, that is at peak pressure, and a second set of readings is taken at the end of the pause period, called the plateau pressure. This second set of readings greatly simplifies solving the equations for patient resistance and compliance if the flow at that time is assumed to be zero. The present system monitors the flow at the end of the pause period and continually adjusts the circuit pressure in order to drive the flow at the end of the pause period to a zero flow value, thus improving the accuracy of the patient resistance and compliance calculation and achieving a more ideal pause pressure profile.

16 Claims, 2 Drawing Sheets

ZERO FLOW PAUSE DURING VOLUME VENTILATION

CROSS REFERENCE TO RELATED APPLICATION

This application claims the priority of U.S. Provisional Application, Serial No. 60/027,613, filed Oct. 10, 1996.

BACKGROUND OF THE INVENTION

This invention relates to medical ventilators for providing breaths to a patient and, more particularly, to a ventilator having a system to provide a zero flow condition during a pause phase following a mechanical inspiration.

Medical ventilator systems are used to support the respiration of patients in acute care situations and in conjunction with the administration of anesthesia to patients undergoing surgical procedures. Often, these ventilators employ an inspiratory pause period following a mechanical inspiration, which has a beneficial physiologic advantage of improving patient oxygenation under certain conditions. In addition, the pause phase allows the clinician to obtain certain physiologic information concerning that patient, specifically, it is useful to determine measures of the patient's lung compliance and airway resistance as valuable data in evaluating the patient.

Basically, the lung compliance is an indication of the springiness or elasticity of the lungs and the airway resistance is the pneumatic resistance of the patient's airways from the mouth where the ventilator is connected to the internal volume of the lungs. A determination of the lung compliance and resistance through use of a pause is typically accomplished through the use of the following equation derived from a simple linear model:

$$P_{AW} = Q_{AW} * R_{PAT} + \frac{V_T}{C_{PAT}}$$

Where
$P_{AW}$ is the Patient Airway Pressure
$Q_{AW}$ is the Patient Airway Flow
$R_{PAT}$ is the Patient Airway resistance
$C_{PAT}$ is the Patient Lung Compliance and
$V_T$ is the delivered Tidal Volume The values for the equation are taken during the normal inhalation of the lungs and the values are generally selected at two points, one at the end of the inspiration where the patient pressure is at a peak, $P_{MAX}$ and a second condition after the ventilator provides the pause so that the flow to and from the patient is zero. At that point, the patient airway pressure sample is termed $P_{PLATEAU}$. Thus, by taking data at two points, there are two equations and two unknowns allowing the the lung compliance and the airway resistance of the patient to be determined as shown below.

Using the assumption that the patient airway flow ($Q_{AW}$) is zero at the $P_{PLATEAU}$ observation point, the resistance component is observed to drop out of the model equation leaving the term:

$$P_{AW} = P_{PLAT} = \frac{V_T}{C_{PAT}}$$

Thus, using the $P_{PLAT}$ data point along with the volume delivered to the patient ($V_T$), the equation is easily solved for the patient compliance ($C_{PAT}$). With that value thus determined, the pressure ($P_{MAX}$) and flow rate ($Q_{AW}$) obtained at the initiation of the pause period can be used to solve the model equation for the patient airway resistance. In this fashion, the clinician can readily determine measures of the patient airway resistance and the lung compliance.

In using the plateau pressure value for solving this equation however, an inaccuracy is introduced if, in fact, the flow to and/or from the patient is not truly at a zero flow condition at the end of the pause period. This could occur for a number of reasons. In some ventilator systems, fresh gas is continually being added to the patient circuit even after the end of the inspiratory cycle and thus there is a continual flow of gas to the patient during and after the ventilator pause period. Also, at the end of inspiration, the patient circuit acts as a large reservoir of gas. This gas, being at a higher pressure than the patient's lung pressure, can continue filling the patient's lungs during the pause period, thus again, the data obtained at the end of the pause period does not represent true zero flow conditions.

Accordingly, it would be advantageous in carrying out the foregoing calculations, to insure that the $P_{PLATEAU}$ is determined at zero flow conditions where it truly represents the patient's lung pressure. In addition, ensuring that zero flow is achieved during the pause phase provides the patient with a quality of inspiratory pause that conforms with the ideal representation expected by clinicians, and may have improved clinical efficacy.

SUMMARY OF THE INVENTION

The system of the present invention therefore corrects the aforedescribed problem by providing a system for ensuring that zero flow conditions exist at the end of the pause period. Thus, the airway pressure at that point, the plateau pressure is the same as the pressure within the patient's lungs.

In carrying out the invention, a ventilator system as described in U.S. Pat. No. 5,315,989 may be utilized and that system can determine the flow at the patient airway in order to provide an input to a controller. This controller uses the ventilator drive pressure to control the flow to a zero flow condition at the end of the pause period. In using a flow signal, a preferred algorithm continually senses that flow and readjusts the control pressure in the patient exhalation circuit until the zero flow conditions are attained. By use of the ventilator drive pressures in this manner, the operator is assured that a zero flow condition is met at the end of the pause period. Thus, accurate determinations can be made of the airway resistance and lung compliance and a more ideal pause profile is achieved.

Other objects, features and advantages of the present invention will be more readily apparent from the detailed description of the preferred embodiment set forth below, taken in conjunction with the accompanying drawings.

DESCRIPTION OF THE PREFERRED EMBODIMENT

Figure 1:
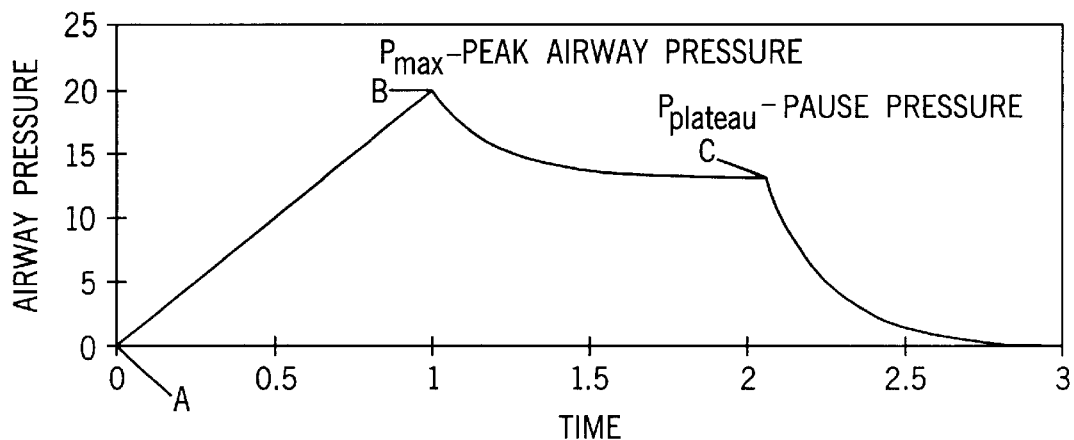
FIG. 1 is a pressure diagram for a typical airway profile of a volume inhalation with a pause period.

Referring now to FIG. 1, there is shown a pressure diagram for a typical airway pressure profile during a volume inspiratory cycle including a pause period. In particular, as can be seen, when the inspiratory cycle progresses, the pressure rises from the zero point at point A to the $P_{MAX}$ at point B which is the measured airway pressure at the end of inspiration. The value of $P_{MAX}$ is thus measured at the end of the inspiratory cycle and the airway flow ($Q_{AW}$) can be determined from the ventilator settings or supplied by the ventilator. The pause period takes place between the $P_{MAX}$ at point B and the end of the pause at point C where the airway pressure is reduced to $P_{PLATEAU}$ which, again, is a measured value. At this point, flow in the patient airway $Q_{AW}$ is considered to be zero in order to solve the equations of the resistance/compliance lung model.

Figure 2:
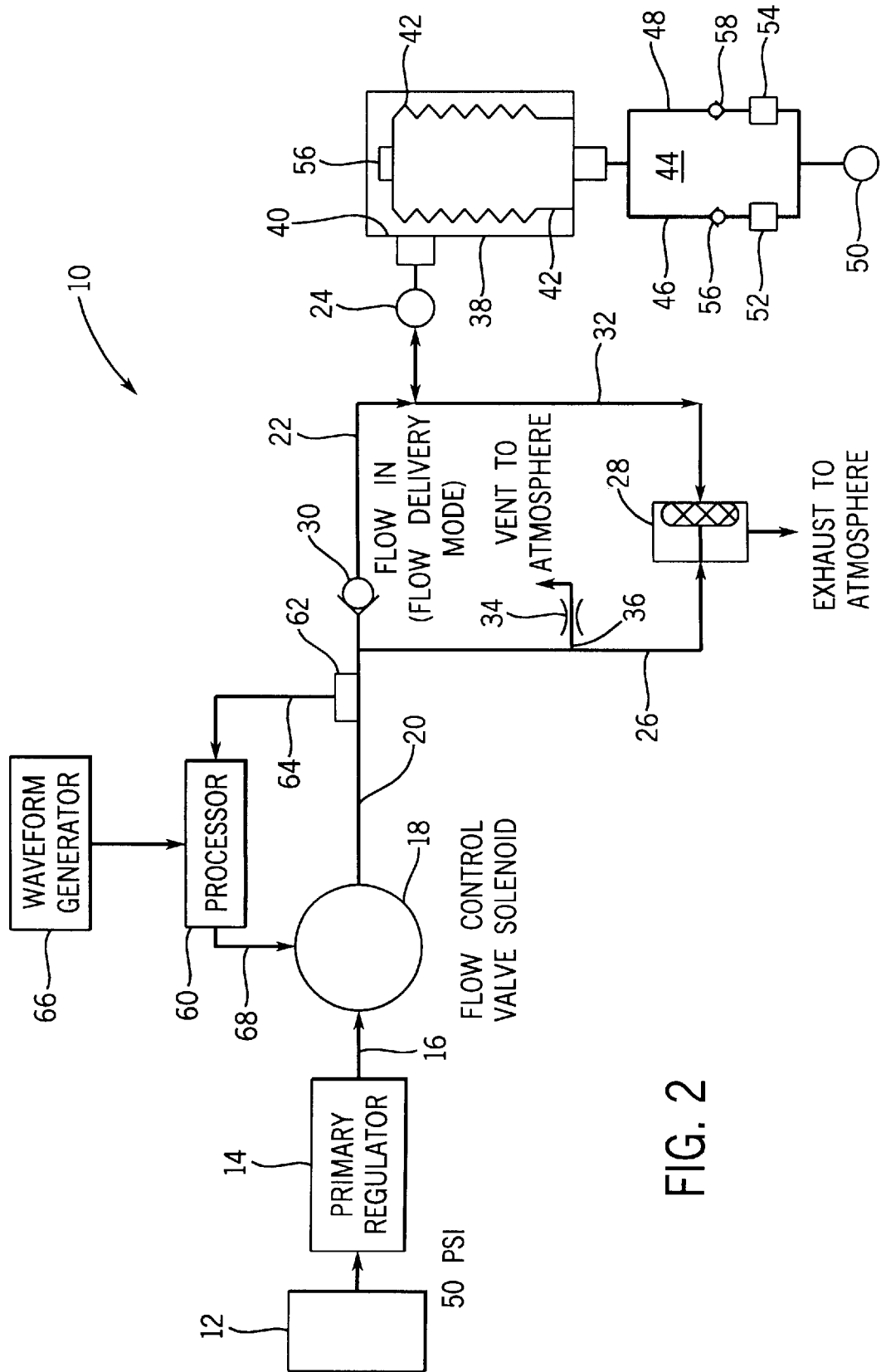
FIG. 2 is a schematic view of a ventilator apparatus suitable for carrying out the present invention.

Referring now to FIG. 2 there is shown a schematic view of a ventilator apparatus suitable for carrying out the present invention. The mechanical aspects of the ventilator apparatus are similar to those disclosed in U.S. Pat. No. 5,315,989 of Tobia and the disclosure of which is incorporated herein by reference, however, there are some differences in the systems and such differences will become apparent from the following description.

Ventilator 10 comprises a gas source 12 which typically provides gas at about 50 psi through a primary regulator 14 to source conduit 16 and which thus supplies flow control valve 18 with gas at approximately 25 psi. Flow control valve 18 is preferably a proportional solenoid valve and which controls the magnitude of gas flow into conduit 20. Conduit 22 communicates with conduit 20 and provides an inspiratory flow branch to ventilator connection 24. An expiratory flow branch is provided by conduit 32 which functions to convey gas from ventilator connection 24 to expiratory valve 28. Check valve 30 is located in conduit 22 to prevent flow from conduits 22 and 32 into conduit 20 during expiration of gas from ventilator connection 24.

Expiratory valve 28 controls the pressure and flow through conduit 32. Expiratory valve 28 is preferably a diaphragm or balloon type of valve which is capable of controlling the pressure in conduit 32 according to a reference pressure. Reference control pressure is provided to expiratory valve 28 via the pressure control conduit 26. A flow restrictor 34 is provided on vent conduit 36 to provide a bleed for the pressure control conduit 26. When gas pressure in expiratory conduit 32 exceeds the reference pressure in conduit 26, gas is exhausted from expiratory conduit 32 through expiratory valve 28 to the atmosphere. Thus, the pressure in expiratory conduit 32 is controlled by the reference pressure in pressure control conduit 26 which, in turn, is controlled by the output of the flow control valve 18.

Ventilator connection 24 is made to a bellows assembly 38 and conduit 22 communicates with the bellows outer chamber 40 to actuate bellows 42. The patient's breathing circuit 44 is in communication with the interior of the bellows 42 and thus is isolated from the gas in the ventilator 10.

Patient breathing circuit 44, as shown is a circle system comprising an inhalation limb 46 and an exhalation limb 48 that delivers breathing gas to and receives exhaled gas from, respectively, patient connection 50. An inspiratory flow sensor 52 is located in the inhalation limb 46 and an expiratory flow sensor 54 is located in the exhalation limb 48 to monitor the flow in the inhalation and exhalation limbs 46,48, that is the flow to and from the patient connection 50. As also can be seen, there are check valves 56 and 58 to insure that the flow in the inhalation limb 46 as well as the exhalation limb 48 is maintained in the proper direction.

Both the inspiratory flow sensor 52 and the expiratory flow sensor 54 monitor flow and communicate signals representative of that flow to the processor 60 as will be explained.

Pressure sensor 62 communicates with the interior of conduit 20 and provides a signal indicative of the pressure within circuit 20 to processor 60 via a signal line 64. The pressure in conduit 20 will be referred to as the manifold pressure or $_{MAN}$ and, as can be seen, is indicative of the pressure within pressure control conduit 26. Processor 60 includes a microprocessor connected via an electronic bus to read only memory (ROM) and random access memory (RAM) in a known digital computer configuration. Waveform generator 66 provides a desired waveform to processor 60. Flow control valve 18 is controlled by the processor 60 via a control signal line 68 to track the desired pressure waveform established by the user.

Conduits 20, 22 and 32 thus define a ventilator circuit which communicates with the ventilator connection 24. During the inspiratory phase of a volume ventilation patient breath, the ventilator 10 operates in the flow delivery mode whereby flow is delivered from gas source 12 through the flow control valve 18 to conduits 20 and 22 and finally to the ventilator connection 24. During most of the expiratory phase of the patient breath, check valve 30 prevents flow from conduit 22 to conduit 20 and gas flows via conduit 32 to expiratory valve 28 where it is exhausted to the atmosphere. The ventilator thus operates in a flow exhaust mode.

In order to maintain a positive pressure at ventilator connection 24 during the pause phase of the breath cycle, the flow control valve 18 is adjusted so as to maintain a small amount of flow exhausting across flow restrictor 34. Thus, pressure is generated in pressure control conduit 26 which serves to bias shut expiratory valve 28, holding pressure in expiratory conduit 32, ventilator connection 24 and concomitantly at the patient connection 50. By controlling the flow output of the flow control valve 18 in response to signals from the inspiratory flow sensor 52 and expiratory flow sensor 54, the pressure at patient connection 50 can be controlled such that a zero flow state exists at patient connection 50 at the point in time that the pause period ends.

With the present system, the prior model assumption that the flow is zero at the end of the pause period is assured by adjusting the circuit pressure during the pause period so as to drive the end of the pause flow to converge on zero. Thus, the $P_{AW}$ measured at the end of the pause period is, in fact, equal to the patient lung pressure.

Figure 3:
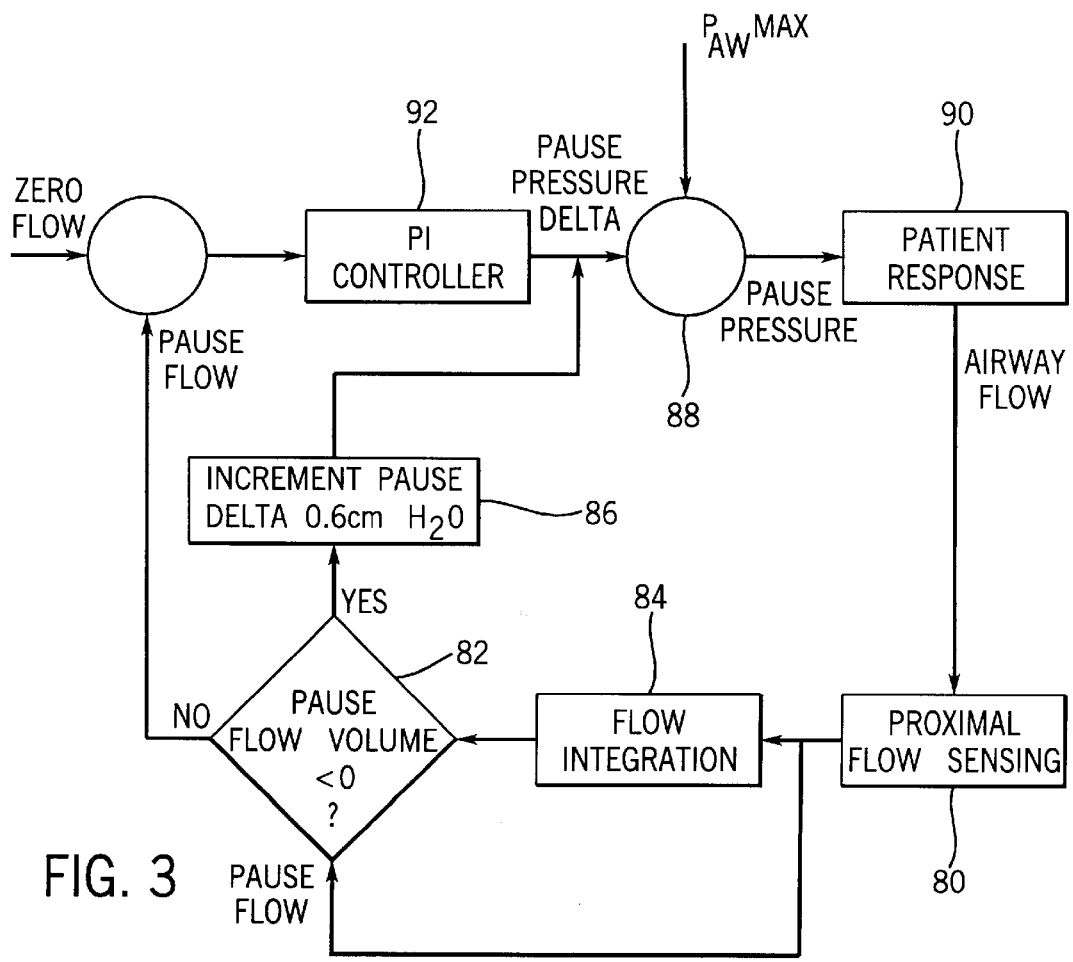
FIG. 3 is a flow chart of a system used to produce a zero flow condition in the patient circuit at the patient airway.

Turning now to FIG. 3, there is shown a flow chart of the preferred method of assuring a zero flow at the end of the pause period. Taking the steps of the flow chart, there is a proximal flow sensing block 80 that receives information from a flow sensor that monitors the flow to and from the patient during the pause period. That flow can be positive indicating that there was a flow to the patient or may be negative indicating that a flow was received from the patient. Obviously, the flow sensor may be as shown in FIG. 2 where two sensors are utilized, or a single bi-directional flow sensor may be used in the patient airway.

When it is determined that volume is not being exhausted from the patient during the pause period, via flow integration 84 and decision block 82, data from the proximal flow sensing block 80 is passed to a standard PI (proportional-integral) controller 92. The PI controller 92 adjusts a Pause Pressure Delta on a breath to breath basis. That Pause Pressure Delta is added to the previous breath's $P_{MAX}$ that is continuously monitored in the ventilator in order to provide a target pressure (Pause Pressure) to be held by the expiratory valve (FIG. 2) during the pause period. In this way, the PI controller 92 is able to cause a pause pressure to be applied to the expiratory valve which produces a zero flow, end pause condition at the patient airway. Accordingly, for each breath, the pause pressure may change through an adjustment of the Pause Pressure Delta. This adjustment may increase the pause pressure to the expiration valve, resulting in higher (more positive) end pause flows to the patient, or may decrease the pause pressure, thereby resulting in lower (more negative) flow at the end of the pause period.

In certain circumstances, it is possible for a zero flow, end pause condition to exist even though a significant amount of flow has been released from the lungs earlier in the pause period. For example, with a very negative pause delta and a long pause period, a period of partial exhalation may occur earlier in the pause period but be stabilized to zero flow at the end of the pause period. In order to handle that situation, the delivered volume during the pause period is integrated at flow integration block 84. The decision block 82 thus determines if the pause flow volume is less than zero volume and if it is determined to be so, the PI controller is bypassed and the Pause Pressure Delta is incremented by a preset or calculated amount, determined in block 86, which is independent of the flow sensed in block 80.

Once a pause pressure is established on the exhalation valve, patient flow at the end of the pause period occurs as a function of the patient and circuit response characteristics represented in block 90. Accordingly, by use of the closed loop, the system will eventually reach a state of zero flow at the end of the pause period.

While the present invention has been set forth in terms of a specific embodiment, it will be understood that the ventilator and bellows system herein disclosed may be altered or modified by those skilled in the art to other configurations. Accordingly, the invention is to be broadly construed and limited only by the scope and spirit of the claims appended hereto.

We claim:

1. A ventilator system for a patient circuit providing breathing gas to a patient connected to the patient circuit during an inhalation phase of a breath and receiving exhaled gases from a patient in an exhalation phase of a breath, said ventilator system providing an indication of the pressure in the patient's lungs, said ventilator system comprising:
   a ventilator;
   a drive conduit fluidly connecting said ventilator to the patient circuit for allowing said ventilator to increase the pressure in the patient circuit to deliver a quantity of breathing gas through the patient circuit to the patient in the inhalation phase and to reduce the pressure in the patient circuit to allow breathing gas to be exhaled by the patient during the exhalation phase, said ventilator further providing a pause period following the inhalation phase;
   a flow sensor in the patient circuit for sensing the presence of a gas flow to or from a patient in the patient circuit during the pause period, said sensor providing a signal indicative of the sensing carried out by the sensor;
   exhalation pressure control means for altering the pressure in the patient circuit during the exhalation phase;
   processor means for controlling said pressure control means within the pause period to provide a controlled reduction of pressure in the patient circuit during the pause period of a given breath, said processor means receiving the signal from said flow sensor and operating said exhalation pressure control means in a subsequent breath of the patient, in the event gas flow is sensed in the given breath, to alter the controlled pressure reduction in the subsequent breath in a manner tending to reduce the flow of gas to or from the patient to zero by the end of the pause period; and
   means for obtaining a pressure measurement indicative of that in the patient circuit, a pressure measurement taken when gas flow in the patient circuit is zero comprising an indication of the pressure in a patient's lungs.

2. A ventilator system as defined in claim 1 wherein said processor means operates said exhalation pressure control means incrementally after each breath based on said signal from said flow sensor indicative of gas flow in the patient circuit.

3. A ventilator system as defined in claim 2 wherein said processor means is further defined as integrating said flow sensor signal during said pause period to determine a pause period flow volume and evaluates said pause period flow volume to determine the incremental operation of said exhalation pressure control means.

4. A ventilator system as defined in claim 2 wherein said processor alters the pressure incrementally in said patient circuit by means of a proportional integral controller.

5. A ventilator system as defined in claim 1 wherein said patient circuit has an inspiratory limb and an expiratory limb and said flow sensor comprises a flow transducer monitoring the flow in said inspiratory limb and a flow transducer monitoring flow in said expiratory limb.

6. A ventilator system as defined in claim 1 wherein said flow sensor comprises a single flow transducer intermediate said patient circuit and a patient, said flow transducer measuring both the inspiratory flow to, and expiratory flow from, a patient.

7. A ventilator system as defined in claim 1 wherein said processor means is further defined as operating said exhalation pressure control means to provide a more rapid reduction in pressure in the patient breathing circuit in a subsequent breath when said flow sensor senses a flow of gas to a patient.

8. A ventilator system as defined in claim 1 wherein said processor means is further defined as operating said exhalation pressure control means to provide a less rapid reduction in pressure in the patient breathing circuit in a subsequent breath when said flow sensor senses a flow of gas from a patient.

9. A method for providing an indication of the pressure in the lungs of a patient, said method comprising the steps of:
   (a) increasing the pressure in a patient circuit adapted for connection to a patient to deliver breathing gas through the patient circuit to a patient during an inhalation phase of a given breath of the patient;
   (b) stopping the pressure increase in the patient circuit to initiate a pause period in the breath;
   (c) providing a controlled reduction of pressure in the patient circuit during the pause period;
   (d) at a point in time following commencement of the controlled pressure reduction, sensing whether there is a flow of gas to or from a patient in the patient circuit;
   (e) if gas flow is not present, obtaining a measurement of the pressure in the patient circuit as the indication of patient lung pressure; and
   (f) if gas flow is present, establishing an altered pressure reduction for the patient circuit for use in the pressure alteration to be carried out in the pause period of a subsequent breath of the patient, the altered pressure reduction being one tending to reduce gas flow to or from the patient to zero.

10. A method as defined in claim 9 wherein the pressure in the patient circuit is controlled by a pressure controlled exhalation valve and said step of providing a controlled reduction of the pressure in the patient circuit is further defined as providing an alteration of the pressure on the exhalation valve.

11. A method as defined in claim 9 wherein the step of sensing whether there is a flow of gas further comprises sensing and integrating the flow of gas in the patient circuit in the pause period.

12. A method as defined in claim 9 wherein the step of establishing the altered pressure reduction for a subsequent breath is further defined as incrementally altering the reduction in pressure.

13. A method as defined in claim 12 wherein the step of sensing whether there is a flow of gas further comprises sensing and integrating the flow gas in the patient circuit in the pause period.

14. A method as defined in claim 9 further including the step of reducing the pressure in the patient circuit at the end of the pause period to a level sufficient to allow breathing gas to be exhaled by the patient during an exhalation phase.

15. A method according to claim 9 wherein step (f) is further defined as establishing a more rapid pressure reduction for the patient circuit if there is gas flow to a patient in a patient circuit.

16. A method according to claim 9 wherein step (f) is further defined as establishing a lesser pressure reduction for the patient circuit if there is gas flow from a patient in a patient circuit.

* * * * *